United States Patent [19]
Norgren

[11] 3,943,927
[45] Mar. 16, 1976

[54] INJECTION APPARATUS

[76] Inventor: Robert S. Norgren, 2840 N.W. 144th, Beaverton, Oreg. 97005

[22] Filed: Mar. 3, 1975

[21] Appl. No.: 554,686

[52] U.S. Cl. ............................ 128/218 D; 128/216
[51] Int. Cl.² ............................................ A61M 5/00
[58] Field of Search ...... 128/218 R, 218 P, 218 PA, 128/218 N, 218 D, 218 DA, 218 F, 214, 215, 216, 221, 220

[56] References Cited
UNITED STATES PATENTS

| | | | |
|---|---|---|---|
| 2,591,706 | 4/1952 | Lockhart | 128/218 D |
| 2,688,965 | 9/1954 | Huber | 128/218 D |
| 2,871,856 | 2/1959 | Steiner | 128/216 |
| 3,702,609 | 11/1972 | Steiner | 128/218 F |

Primary Examiner—John D. Yasko
Attorney, Agent, or Firm—Adrian J. LaRue

[57] ABSTRACT

An injection apparatus includes a housing having an ampule provided with medication therein, a needle at one end and a sealing piston in the other end of the ampule, the ampule disposed in position in one part of the housing, the second part of the housing is provided with first means for moving the ampule so that the needle extends out from the housing and into a body against which the housing is positioned as the second part is moved relative to the first part and second means for moving the piston in the ampule to express the medication therefrom into the body upon further movement of the second housing part relative to the first housing part.

8 Claims, 4 Drawing Figures

INJECTION APPARATUS

BACKGROUND OF THE INVENTION

Bee stings can be fatal to persons who are allergic to such stings if they do not receive an antitoxin within a short period after they have been stung by a bee. Thus, these people have to take proper precautions to have readily available or be in close proximity to an injection device in order to inject themselves or be injected with the antitoxin within the required time to save their lives. This is true also with regard to other bites, allergic reactions, asthmatics and allied problems.

A typical kit consists of a conventional syringe and a rubber-sealed container containing the antitoxin or a loaded syringe. Several drawbacks to this kit are noteworthy. The needle of the syringe has to be inserted through the rubber seal, the antitoxin has to be drawn into the syringe, aspirated and then injected into the body. This can be difficult for a person under emotional stress who is in emminent danger of losing his or her life unless the antitoxin is administered in time, because the container could be dropped and broken before being drawn into the syringe, the syringe could be broken, and, if aspiration of the syringe is not properly done, air could be injected into the body causing serious harm. Moreover, the mecessity of having to carry the syringe and antitoxin container can be difficult and subject them to breakage.

Complicated syringes using spring release mechanisms such as disclosed in U.S. Pat. Nos. 3,543,603; 3,496,937; 2,856,924; 3,702,609 and 3,742,948 can be used, but these are expensive and susceptible to being accidentially actuated thereby not being available for emergency use.

SUMMARY OF THE INVENTION

The present invention relates to an injection apparatus and more particularly to an injection apparatus for emergency situations.

An object of the present invention is to provide an injection apparatus including means for moving an ampule within a housing to a first position exposing the needle and a second position expressing the medication from the ampule.

Another object of the present invention is the provision of an injection apparatus wherein the housing thereof includes guide means along which the ampule moves and for guiding the ampule driving means out of engagement therewith upon the ampule reaching the first position.

A further object of the present invention is to provide an injection apparatus which includes a transparent housing to discern the condition of the ampule therein.

An additional object of the present invention is the provision of an injection apparatus including a two part housing with the parts telescopically movable relative to each other and which are provided with sealing means therebetween.

The foregoing and other objects of the invention will appear more fully from the following description and the accompanying drawing illustrating a preferred embodiment of the invention. It is to be understood that changes may be made from the exact details shown and described without departing from the principles of the invention.

DETAILED DESCRIPTION OF THE INVENTION

Turning now to the drawings an injection apparatus IA is illustrated which comprises a housing 10 including an ampule-holding section 12 and an operating section 14. Housing 10 is preferably molded from a suitable plastic material; it can be of any desired color, but it is preferable that it is transparent.

Figure 2:
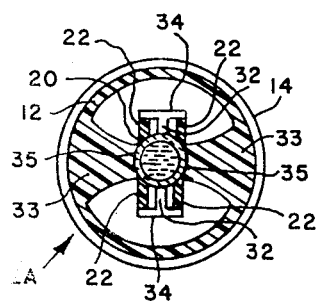
FIG. 2 is a view taken along lines 2—2 of FIG. 1.

Ampule-holding section 12 has a relief area 16 in the bottom to enable needle 18 of ampule 20 to readily penetrate therethrough when ampule 20 is moved to its operative position as shown in FIG. 2. Spaced pairs of guide members 22 extend outwardly from the bottom of section 12 on opposite sides of relief area 16 and they receive ampule 20 therebetween. Projections 24 are provided on the inner surfaces of guide members 22 and they are disposed in a necked-down section 26 of ampule 20 to maintain ampule 20 in position so that ampule 20 does not move forward causing needle 18 to puncture relief area 16 accidentially. Projections 24 will however be deformed when ampule 20 is moved forward as will be explained hereafter. Guide members 22 are provided with beveled surfaces 30 at their free ends. Diametrical extensions 33 are provided by section 12 and they have arcuate surfaces 35 at their inner ends to provide additional guide means for ampule 20.

Ampule-driving members 32 extend outwardly from the bottom of operating section 14 and they move within the respective spaced pairs of guide members 22 when section 14 is moved relative to section 12. Cross arms 34 are located at the free ends of ampule-driving member 32. Ampule-driving members 32 normally engage the inner end of ampule 20.

A radiused projection 36 is provided on the outer surface of section 12 which normally mates with a recess 38 on the inner surface of section 14 to maintain these sections in a normally-inoperative position and to provide a seal therebetween so that housing 10 is hermetically sealed to protect needle 18. Alternatively, an O-ring of suitable conventional sealing material can be disposed in recesses in sections 12 and 14 to provide the sealing condition.

Figure 1:
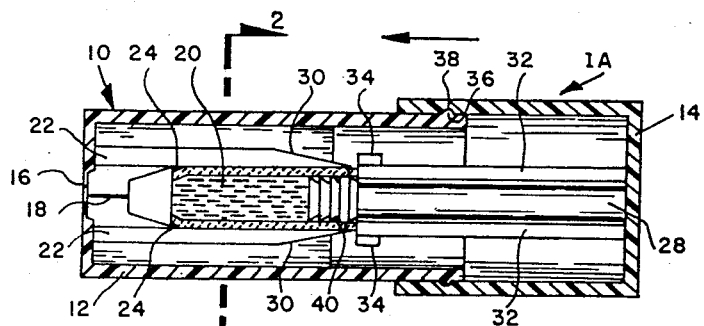
FIG. 1 is a cross-sectional view illustrating the injection apparatus in its normally inoperative position.
Figure 3:
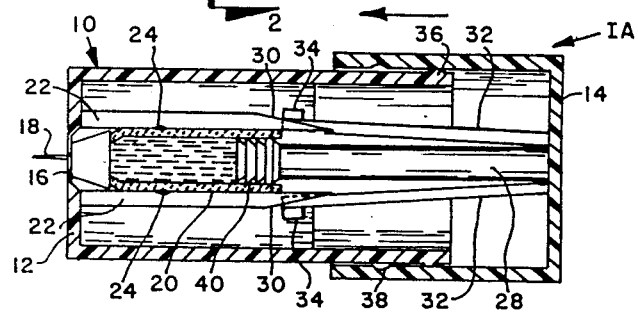
FIG. 3 is a view similar to FIG. 1 illustrating the ampule moved to a first position by movement of the housing parts relative to each other.
Figure 4:
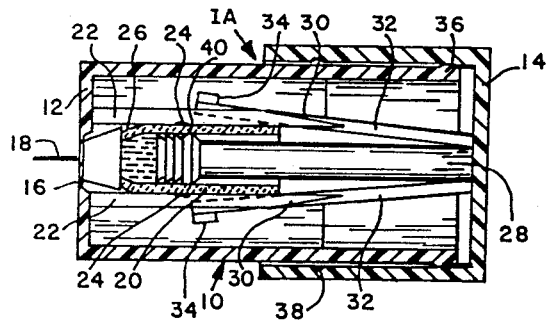
FIG. 4 is a view similar to FIG. 1 illustrating the expressing of the medication from the ampule.

In operation after a person has been stung by a bee, insect or bitten by a snake, housing 10 is placed against an area of the person's body, preferably against the arm adjacent the shoulder, pressure is applied to section 14 whereby amule-driving members 32 drive ampule 20 along guide members 22 deforming projections 24 and moving ampule 20 to a first position so that needle 18 punctures relief area 16 as shown in FIG. 3 and penetrates the exidermis of the body area to inter muscular area. Arms 34 engage beveled surfaces 30 of guide members 32 and move or cam ampule-driving members 32 out of engsgement with the end of ampule 20 when ampule 20 has reached the first or needle operating position whereupon plunger 28 engages sealing piston 40 and moves it along ampule 20 thereby expressing the medication therein into the body of the afficted person as shown in FIG. 4, arms 34 moving along beveled surfaces 30 and the outer edges of members 22 while members 32 move between respective spaced pairs. Guide members 22 providing guide means along which ampule 20 is moved and along which arms 34 move.

As can be discerned, a unique and novel injection apparatus has been disclosed to be readily utilized by persons in danger of being stung by bees, wasps, insects or the like and which is simple in construction and easily operated to inject life-saving antitoxin into the body. Although the invention has been explained and illustrated with reference to a particular embodiment, it is to be appreaciated that various adaptations and modifications may be made without departing from the appended claims.

The invention is claimed in accordance with the following:

1. An injection apparatus for injection of a medication from an ampule and into a person's body comprising:
    a housing including an ampule-receiving section and an operating section, an ampule having a piston therein and a needle thereon disposed in said ampule- receiving section, said operating section being movable relative to said ampule-receiving section;
    guide means provided by said ampule-receiving section along which said ampule is disposed;
    ampule-driving means and plunger means provided by said operating section, said ampule-driving means driving a ampule along said guide means to a first position in said housing when said operating section is moved relative to said ampule-receiving section upon said housing being positioned against an area of the person's body thereby driving a needle through an end of said housing and into the person's body and said plunger means driving said piston in a ampule to a second position thereby injecting the medicine in the ampule into the person's body; and means provided by said ampule-driving means and said guide means to move said ampule-driving means out of engagement with said ampule when said ampule has reached said first position.

2. An injection apparatus according to claim 1 wherein seal means are provided between said ampule-receiving section and said operating section.

3. An injection apparatus according to claim 1 wherein said housing is transparent.

4. An injection apparatus according to claim 1 wherein said guide means include means for maintaining said ampule in a normally-inoperative position.

5. An injection apparatus according to claim 1 wherein said guide means comprise pairs of spaced members disposed on opposite sides of a central axis of said housing and diametrical extensions having arcuate inner surfaces.

6. An injection apparatus according to claim 5 wherein said ampule-driving means comprise members that move between respective pairs of spaced members when said sections move relative to each other.

7. An injection apparatus according to claim 1 wherein said means for moving said ampule-driving means comprise beveled surfaces on said guide means and arms on said ampule-driving means.

8. An injection apparatus according to claim 1 wherein said ampule-receiving section has a relief area to enable said needle to easily puncture said housing when said ampule is moved to said first position.

* * * * *